(12) United States Patent
Tuli et al.

(10) Patent No.: US 8,444,937 B2
(45) Date of Patent: May 21, 2013

(54) IN-SITU SOIL NITRATE ION CONCENTRATION SENSOR

(75) Inventors: Atac Tuli, Davis, CA (US); Jan W. Hopmans, Davis, CA (US); Tamir Kamai, Davis, CA (US); Benjamin D. Shaw, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/073,551

(22) Filed: Mar. 28, 2011

(65) Prior Publication Data

US 2011/0242530 A1    Oct. 6, 2011

Related U.S. Application Data

(63) Continuation of application No. 12/267,895, filed on Nov. 10, 2008, now Pat. No. 7,927,883.

(60) Provisional application No. 60/986,663, filed on Nov. 9, 2007.

(51) Int. Cl.
| | | |
|---|---|---|
| *G01N 33/24* | (2006.01) | |
| *G01N 1/10* | (2006.01) | |
| *G01N 21/27* | (2006.01) | |
| *G01N 27/333* | (2006.01) | |
| *E21B 49/08* | (2006.01) | |

(52) U.S. Cl.
USPC ....... 422/535; 73/864.74; 175/59; 422/82.01; 422/82.03; 422/82.05; 422/82.09; 422/534; 436/28; 436/110; 436/149; 436/150; 436/151; 436/164; 436/171; 436/172; 436/177

(58) Field of Classification Search
USPC .............. 422/82.01–82.09, 534–535; 436/25, 436/28, 110, 149–151, 164, 171–172, 177–178; 73/863.23, 864.74; 175/21, 59
See application file for complete search history.

(56) References Cited

U.S. PATENT DOCUMENTS

| | | | |
|---|---|---|---|
| 1,643,878 A | | 2/1932 | Gunther |
| 2,878,671 A | * | 3/1959 | Prosser et al. .................... 73/73 |
| 3,028,313 A | | 4/1962 | Oberdorfer et al. |
| 3,181,098 A | * | 4/1965 | Richards ........................ 338/34 |

(Continued)

OTHER PUBLICATIONS

Aldstadt, J.H. et al.—"Analytical Chemistry and the Cone Penetrometer: In Situ Chemical Characterization of the Subsurface"—Mikrochim. Acta, vol. 127, 1997, pp. 1-18.

(Continued)

*Primary Examiner* — Arlen Soderquist
(74) *Attorney, Agent, or Firm* — John P. O'Banion

(57) ABSTRACT

A method and apparatus for near real-time in-situ soil solution measurements is presented. An outer sleeve is placed in soil where ionic concentrations of organic or inorganic species are to be measured. A porous section connects with the outer sleeve (the porous section initially loaded with distilled water) equilibrates with the solution present in soil pores to form a solution to be measured. The initial distilled water is displaced within the porous section by a removable plunger. After substantial equilibration of the solution to be measured within the apparatus, the plunger is removed and a removable probe replaced. The probe may be an Ion Selective Electrode, or a transflection dip probe. The probe then may be used under computer control for measurement of solution properties. The Ion Selective Electrode may measure nitrate ($NO_3^-$) concentrations. The transflection dip probe may be read with spectrometer with an input deuterium light source.

27 Claims, 12 Drawing Sheets

U.S. PATENT DOCUMENTS

| | | | |
|---|---|---|---|
| 3,427,862 A | 2/1969 | Hubner | |
| 3,690,166 A | 9/1972 | Grice et al. | |
| 3,786,675 A | 1/1974 | Delatorre et al. | |
| 3,862,576 A | 1/1975 | Pogorski | |
| 3,864,232 A | 2/1975 | Handman et al. | |
| 3,877,291 A | 4/1975 | Hoppesch et al. | |
| 4,056,969 A | 11/1977 | Barringer | |
| 4,350,051 A | 9/1982 | Thompson | |
| 4,408,481 A | 10/1983 | Sidey | |
| 4,438,654 A * | 3/1984 | Torstensson | 73/864.52 |
| 4,520,657 A * | 6/1985 | Marthaler | 73/73 |
| 4,548,907 A * | 10/1985 | Seitz et al. | 436/163 |
| 4,578,586 A | 3/1986 | Preston | |
| 4,580,440 A | 4/1986 | Reid et al. | |
| 4,669,554 A * | 6/1987 | Cordry | 175/59 |
| 4,696,903 A | 9/1987 | Owen | |
| 4,717,473 A * | 1/1988 | Burge et al. | 210/170.07 |
| 4,745,801 A * | 5/1988 | Luzier | 73/152.23 |
| 4,782,234 A | 11/1988 | Chudyk et al. | |
| 4,804,050 A | 2/1989 | Kerfoot | |
| 4,807,707 A * | 2/1989 | Handley et al. | 175/20 |
| 4,816,161 A * | 3/1989 | Olness et al. | 210/638 |
| 4,843,247 A * | 6/1989 | Yamazoe et al. | 250/573 |
| 4,857,473 A | 8/1989 | Margaritz et al. | |
| 4,938,602 A * | 7/1990 | May et al. | 356/435 |
| 4,998,824 A * | 3/1991 | Littlejohn et al. | 356/407 |
| 5,010,776 A | 4/1991 | Lucero et al. | |
| 5,035,149 A * | 7/1991 | Wierenga | 73/863.23 |
| 5,045,282 A * | 9/1991 | Kritzman et al. | 422/401 |
| 5,046,568 A * | 9/1991 | Cordry | 175/21 |
| 5,065,019 A * | 11/1991 | Darilek et al. | 250/301 |
| 5,083,019 A | 1/1992 | Spangler | |
| 5,128,882 A | 7/1992 | Cooper et al. | |
| 5,146,998 A * | 9/1992 | Cordry et al. | 175/21 |
| 5,150,622 A * | 9/1992 | Vollweiler | 73/864.74 |
| 5,168,765 A * | 12/1992 | Broussard | 73/864.74 |
| 5,209,129 A * | 5/1993 | Jaselskis et al. | 73/864.64 |
| 5,246,862 A * | 9/1993 | Grey et al. | 436/28 |
| 5,299,141 A * | 3/1994 | Hungerford et al. | 702/49 |
| 5,316,950 A | 5/1994 | Apitz et al. | |
| 5,327,981 A * | 7/1994 | Morgan | 175/21 |
| 5,337,838 A | 8/1994 | Sorensen | |
| 5,351,532 A | 10/1994 | Hager | |
| 5,355,739 A | 10/1994 | Cooper et al. | |
| 5,358,057 A | 10/1994 | Peters et al. | |
| H1470 H | 8/1995 | Ewing et al. | |
| 5,439,800 A | 8/1995 | Thompson | |
| 5,442,293 A * | 8/1995 | Lange | 324/332 |
| 5,445,795 A | 8/1995 | Lancaster et al. | |
| 5,465,628 A * | 11/1995 | Timmons | 73/864.34 |
| 5,485,881 A * | 1/1996 | Toon et al. | 166/165 |
| 5,487,431 A * | 1/1996 | Webb | 175/20 |
| 5,497,091 A | 3/1996 | Bratton et al. | |
| 5,548,115 A * | 8/1996 | Ballard et al. | 250/253 |
| 5,567,621 A * | 10/1996 | Tahara et al. | 436/103 |
| 5,635,710 A | 6/1997 | Reed et al. | |
| 5,644,395 A | 7/1997 | Folta | |
| 5,676,820 A | 10/1997 | Wang et al. | |
| 5,739,536 A | 4/1998 | Bucholtz et al. | |
| 5,758,538 A * | 6/1998 | Hubbell et al. | 73/73 |
| 5,759,859 A | 6/1998 | Sausa | |
| 5,794,696 A * | 8/1998 | Gibson et al. | 166/264 |
| 5,798,940 A | 8/1998 | Bratton et al. | |
| 5,804,743 A * | 9/1998 | Vroblesky et al. | 73/863.23 |
| 5,826,214 A | 10/1998 | Lieb et al. | |
| 5,889,217 A | 3/1999 | Rossabi et al. | |
| 5,902,939 A | 5/1999 | Ballard et al. | |
| 5,941,121 A * | 8/1999 | Faybishenko | 73/73 |
| 5,993,743 A | 11/1999 | Nordman et al. | |
| 6,051,437 A * | 4/2000 | Luo et al. | 436/172 |
| 6,085,576 A | 7/2000 | Sunshine et al. | |
| 6,116,353 A * | 9/2000 | Leavell et al. | 175/22 |
| 6,174,497 B1 * | 1/2001 | Roinestad et al. | 422/82.05 |
| 6,196,074 B1 * | 3/2001 | Varhol | 73/863.23 |
| 6,208,940 B1 | 3/2001 | Kram et al. | |
| 6,242,261 B1 | 6/2001 | Schoenau et al. | |
| 6,275,645 B1 | 8/2001 | Vereecken et al. | |
| 6,298,925 B1 * | 10/2001 | Lee et al. | 175/20 |
| 6,360,620 B1 * | 3/2002 | Jensen | 73/864.62 |
| 6,362,741 B1 | 3/2002 | Hickox et al. | |
| 6,378,362 B1 | 4/2002 | Dickinson | |
| 6,385,380 B1 * | 5/2002 | Friedrich et al. | 385/125 |
| 6,395,233 B1 * | 5/2002 | Diamond et al. | 422/527 |
| 6,487,920 B1 | 12/2002 | Robbat | |
| 6,535,283 B1 * | 3/2003 | Heffels et al. | 356/300 |
| 6,615,653 B1 * | 9/2003 | Hocking | 73/152.01 |
| 6,666,068 B2 | 12/2003 | Boyd et al. | |
| 6,717,658 B1 * | 4/2004 | Saini et al. | 356/70 |
| 6,740,216 B2 | 5/2004 | Diakonov et al. | |
| 6,826,972 B2 | 12/2004 | Clark et al. | |
| 6,920,780 B2 | 7/2005 | Hubbell et al. | |
| 6,928,864 B1 * | 8/2005 | Henry et al. | 73/152.54 |
| 6,976,386 B1 * | 12/2005 | Grover et al. | 73/73 |
| 6,978,688 B2 * | 12/2005 | Engebretson | 73/863.23 |
| 7,003,405 B1 | 2/2006 | Ho | |
| 7,131,341 B2 | 11/2006 | Wareham et al. | |
| 7,234,362 B2 | 6/2007 | Shinn et al. | |
| 7,427,504 B2 | 9/2008 | Torgerson et al. | |
| 7,437,957 B2 * | 10/2008 | Jobin et al. | 73/862.581 |
| 7,927,883 B2 * | 4/2011 | Tuli et al. | 436/110 |
| 8,058,885 B2 * | 11/2011 | Caron | 324/694 |
| 2004/0005715 A1 | 1/2004 | Schabron et al. | |
| 2004/0011965 A1 * | 1/2004 | Hodgkinson | 250/461.1 |
| 2004/0089079 A1 * | 5/2004 | Engebretson | 73/863.23 |
| 2005/0122225 A1 * | 6/2005 | Kram et al. | 340/605 |
| 2006/0091319 A1 * | 5/2006 | Steuerwald et al. | 250/373 |
| 2007/0158065 A1 * | 7/2007 | Heller et al. | 166/264 |
| 2008/0030712 A1 * | 2/2008 | Tokhtuev et al. | 356/51 |
| 2008/0283756 A1 * | 11/2008 | Thomson | 250/339.11 |

OTHER PUBLICATIONS

Artigas, J. et al.—"Development of a screen-printed thick-film nitrate sensor based on a graphite-epoxy composite for agricultural applications"—Sensors and Actuators B, vol. 88, 2003, pp. 337-344.

Beltran, A. et al.—"Development of Durable Nitrate-Selective Membranes for All-Solid State ISE and ISFET Sensors Based on Photocurable Compositions"—Electroanalysis, vol. 14, No. 3, 2002, pp. 213-220.

Capitan-Vallvey, L. et al.—"Disposable Receptor-Based Optical Sensor for Nitrate"—Anal. Chem., vol. 77, 2005, pp. 4459-4466.

Dorn, J.G. et al.—"Real-Time, in Situ Monitoring of Bioactive Zone Dynamics in Heterogeneous Systems"—Environ. Sci. Technol., vol. 39, 2005, pp. 8898-8905.

Riga, P. et al.—"Ionic-Equilibrium Time inside Ceramic Cups in Unsaturated Porous Media"—Soil Sci. Soc. Am. J., vol. 62, 1998, pp. 574-579.

Moutonnet, P. et al.—"Simultaneous Field Measurement of Nitrate-Nitrogen and Matric Pressure Head"—Soil Sci. Soc. Am. J., vol. 57, 1993, pp. 1458-1462.

Ahmad et al.—"Non-invasive monitoring of inorganic species in water"—SPIE vol. 2504, 1995, pp. 436-447.

\* cited by examiner

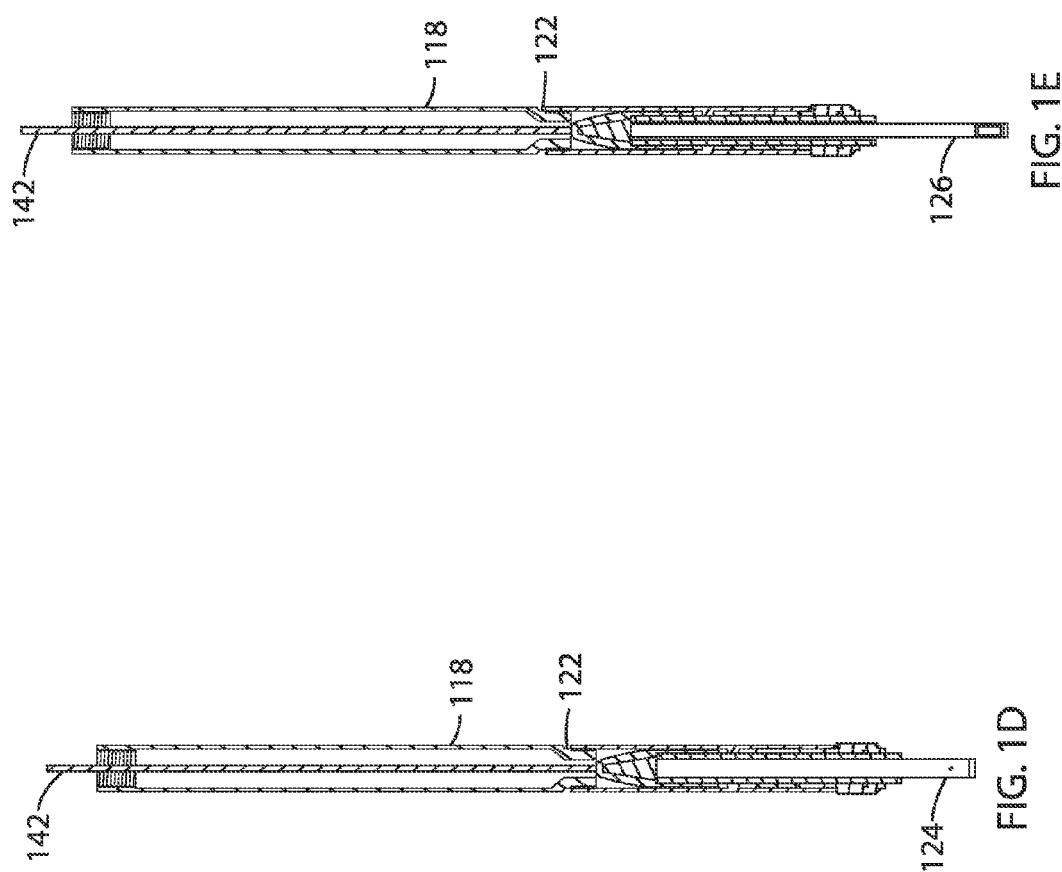

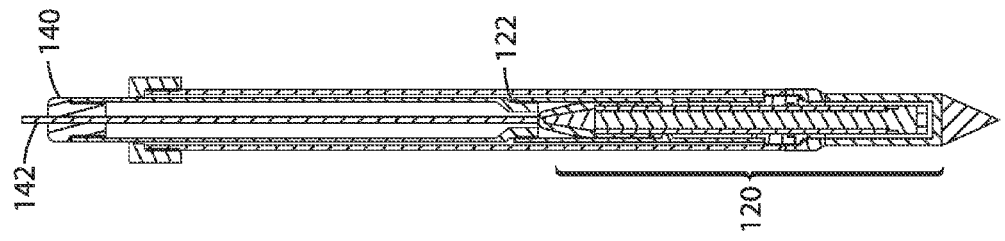
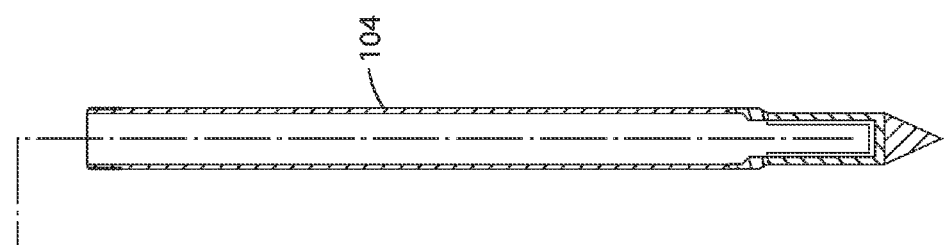
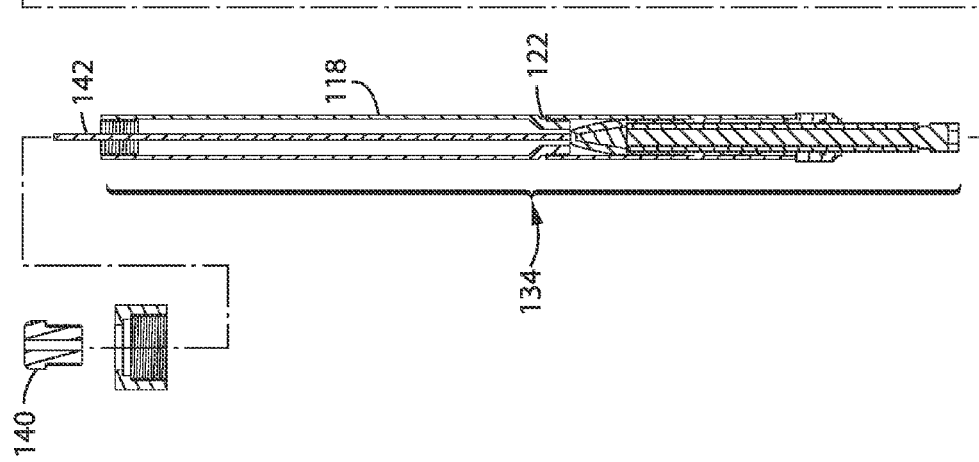

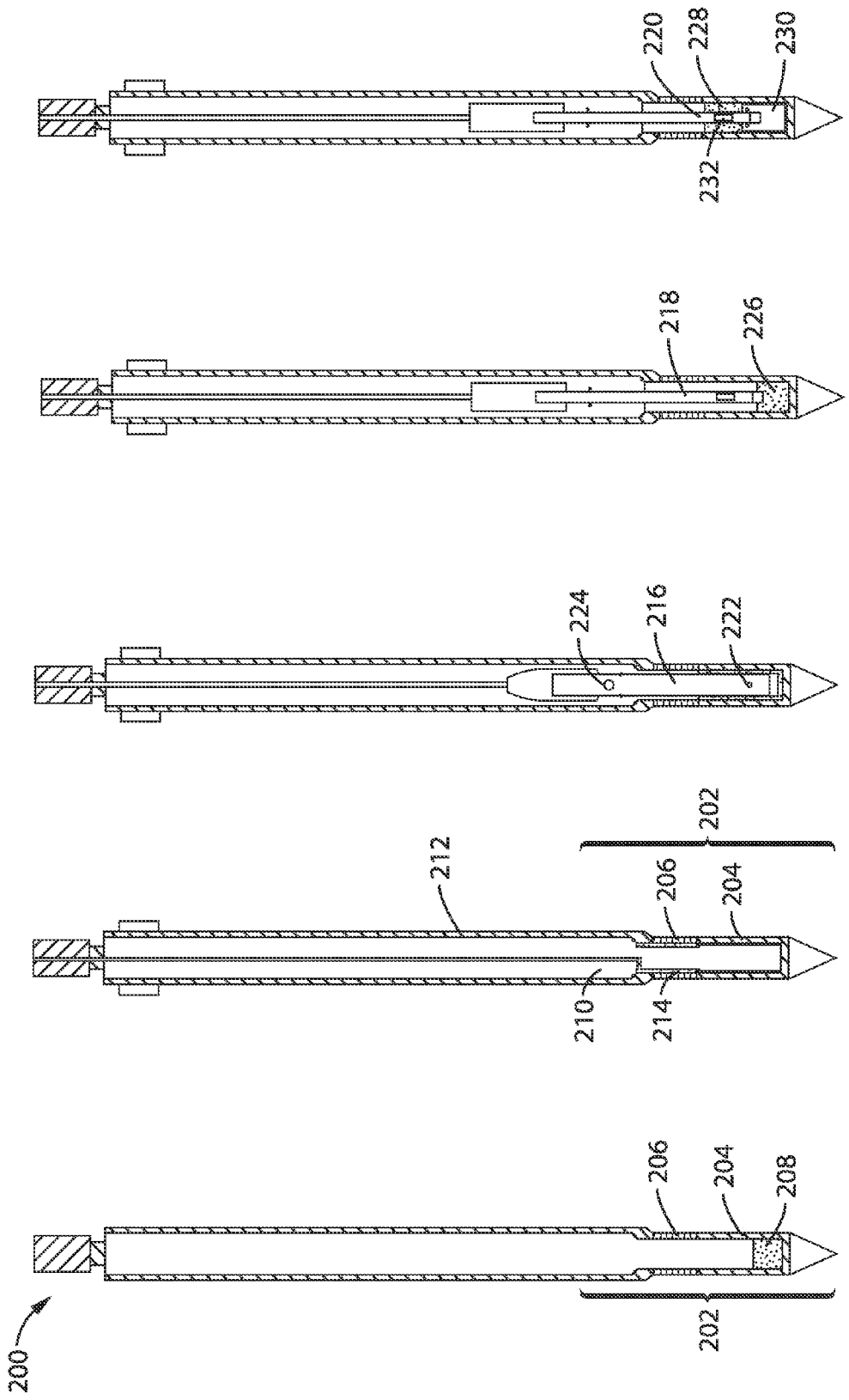

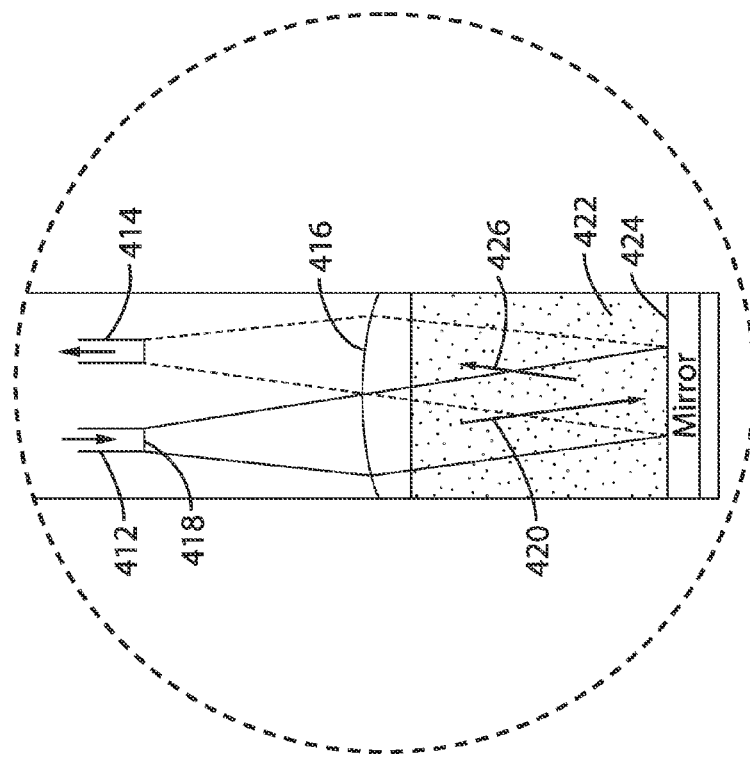
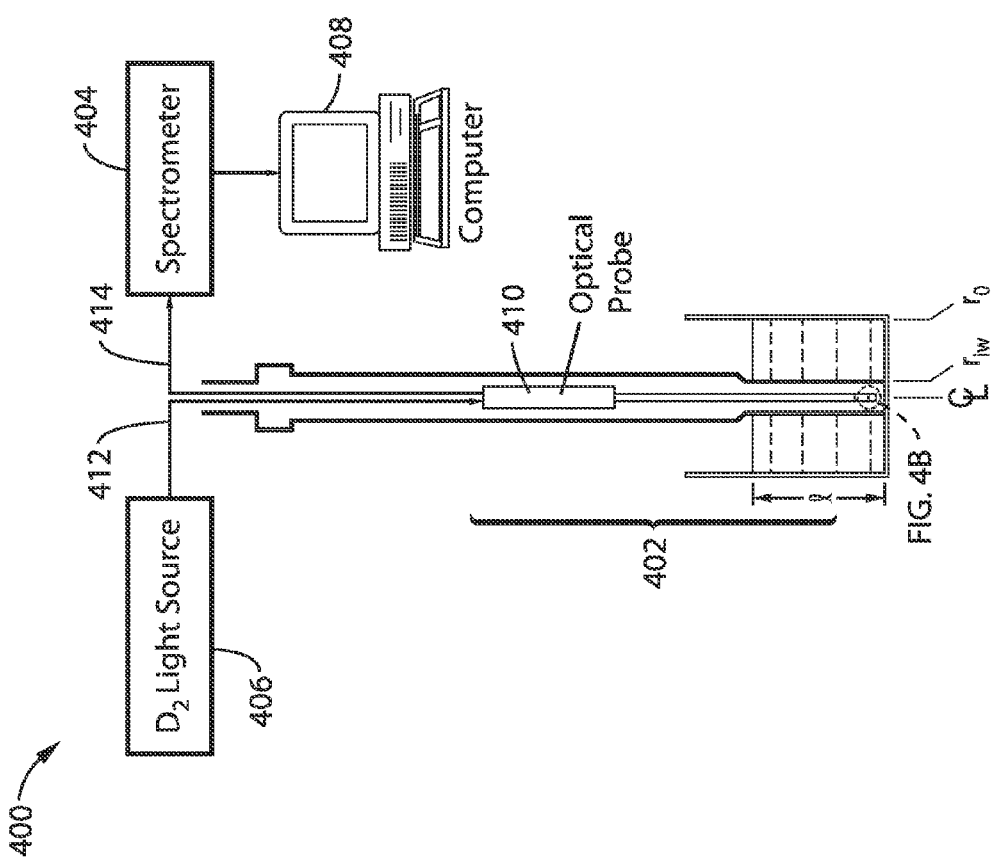
FIG. 4B
FIG. 4A

IN-SITU SOIL NITRATE ION CONCENTRATION SENSOR

CROSS-REFERENCE TO RELATED APPLICATIONS

This application is a continuation of U.S. patent application Ser. No. 12/267,895 filed on Nov. 10, 2008, now U.S. Pat. No. 7,927,883, incorporated herein by reference in its entirety, which claims priority to U.S. provisional patent application Ser. No. 60/986,663 filed on Nov. 9, 2007, incorporated herein by reference in its entirety.

STATEMENT REGARDING FEDERALLY SPONSORED RESEARCH OR DEVELOPMENT

This invention was made with Government support under Grant No. 0410055 awarded by the National Science Foundation. The Government has certain rights in this invention.

INCORPORATION-BY-REFERENCE OF MATERIAL SUBMITTED ON A COMPACT DISC

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. §1.14.

BACKGROUND OF THE INVENTION

1. Field of the Invention

This invention pertains generally to ion concentration measurement, more particularly in-situ soil solution ion measurement, and still more particularly to the real time in-situ measurement of soil nitrate ion concentrations.

2. Description of Related Art

Traditional soil analysis consists of digging up or coring a soil sample of interest, transporting the sample to a laboratory, and then, finally, reading laboratory results. These methodologies are not conducive to real-time or in-situ measurements.

BRIEF SUMMARY OF THE INVENTION

An aspect of the invention is an in-situ probe that comprises: a tube with a distal end; and means for measuring one or more chemical species that enters into the distal end of the tube. The distal end of the tube may contact soil at a porous section of the distal end of the tube. The soil is intact ground soil that is to be measured in-situ. Within the porous section may comprise a solution. The solution is, after a sufficient time for equilibration, a fluid that has the same properties as the fluid present in the interstitial voids between soil particles. Typically such fluid is water with various dissolved ions, and other small particulates in suspension.

The means for measuring may comprise measuring a concentration of an ion in the solution that diffuse or flow into the distal end of the tube through the porous section. The means for measuring may also comprise: an Ion Selective Electrode, or a nitrate Ion Selective Electrode, or an optical probe. Still other probes may be used to determine particulate suspension within the solution. The optical probe may be an Ultraviolet (UV) fiber optic probe.

The optical probe may comprise a transflection dip probe, or other absorption-based probe capable of transmitting an input light source through the sample solution to form an output signal.

Another aspect of the invention is a method of in-situ measurement of solution ion measurement in soil that comprises: a. placing a measurement system, comprising an outer tube sleeve, into a soil that is to be measured, wherein the distal section of the outer tube sleeve comprises a porous section; b. initially contacting a quantity of distilled water with the porous section; c. allowing the quantity of distilled water to equilibrate with the soil to be measured, through the porous section, so as to equilibrate into a solution to be measured; d. contacting the solution with a probe; and then e. measuring the solution with the probe.

The method above may additionally comprise: a. inserting a plunger into the outer tube sleeve, thereby contacting the distilled water with the porous section; and after the solution equilibrates, b. replacing the plunger with the probe. The probe may be comprised of one or more of a group of probes consisting of: an Ion Selective Electrode probe, and a transflection dip probe. Furthermore, the Ion Selective Electrode probe may be a nitrate Ion Selective Electrode probe.

The transflection dip probe discussed above may be capable of measuring absorbance in the range of 235-240 nm, or even 200-1100 nm. Furthermore, the transflection dip probe may specifically measure absorbance at one or more of the wavelengths selected from the group of wavelengths consisting of: 235, 238, and 240 nm.

A still further aspect of the invention is an in-situ ion measurement system, that comprises: a. an outer sleeve tube; b. a porous section attached to the outer sleeve tube, wherein the porous section allows diffusion and bulk fluid flow therethrough; c. a probe placed within the outer sleeve tube, wherein a sensitive portion of the probe contacts a measurement solution that has flowed or diffused through, or equilibrated through, the porous section.

The probe may be an Ion Selective Probe or a nitrate Ion Selective Probe. Other ions may be measured, such as macronutrient ions of: nitrogen, phosphorus, and potassium. Secondary nutrient ions may be measured, such as ions of: calcium, sulfur, and magnesium. Further, micronutrient ions may be measured, such as ions of: boron, chlorine, manganese, iron, zinc, copper, molybdenum, and selenium. Common soil components may also be measured for ions of: calcium, magnesium, potassium, and sodium. Other ions inimical to human and animal life may be measured, such as: arsenic, cadmium, and uranium.

Furthermore, the probe may be a transflection dip probe. The transflection dip probe allows absorption of an input light source to pass through the measurement solution to form an output signal. The input light source may be created by a deuterium light source. Any other light source that illuminates optical absorption spectra of a target ion may also be used. An optical spectrometer may be used to measure an output signal from the transmission of the input light source through the solution.

By suitable design choices, it may be possible to construct a probe that simultaneously measures a plurality of ion concentrations, either with a plurality of Ion Selective Electrodes, or with one or more Ion Selective Electrode and one or more transflection dip probes. Additionally, by suitable design, the transflection dip probe may have a sufficiently broad measurement range to allow concentration measurements of a plurality of concentrations.

A transflection dip probe may be used for in-situ monitoring of groundwater or vadose zone plumes. Within such aqueous sources, contaminants such as benzene, toluene, ethyl benzene, xylenes, styrenes (the foregoing collectively referred to as BTEXS), and or other organic solvents (in either aqueous or non-aqueous phases) may be measured.

In still other applications, in-situ measurements may be used for the monitoring of alcoholic fermentation for wine and beer making by sampling alcohol, sugar, or both concentrations.

A computer may be used to control a collection of in-situ measurements through the spectrometer. These spectrometer measurements may be ion concentration measurements, or more specifically they may be nitrate ion concentration measurements. The process of sequentially collecting a series of measurements using the in-situ apparatus may be stored as a program executable on a computer readable medium.

The in-situ spectrometer measurements may be measured on one or more components of BTEXS. BTEXS may comprise one or more of a contaminant selected from a group of contaminants consisting of: benzene, toluene, ethyl benzene, xylene, and styrene.

The in-situ spectrometer measurements may comprise one or more of a contaminant selected from a group of contaminants consisting of: a polychlorinated biphenyl, tetrachloroethylene, sulfur dioxide, arsenic, selenium, petroleum, petroleum distillates, petroleum byproducts, hydrocarbon, pentachlorophenol, creosote, a pesticide, a polycyclic aromatic hydrocarbon (PAH), a volatile organic carbon (VOC), a dioxin, a dibenzofuran, copper, lead, zinc, hexavalent chromium, cadmium, and mercury.

Further aspects of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWINGS

The invention will be more fully understood by reference to the following drawings which are for illustrative purposes only:

FIG. 1D is a sectioned side view of an Ion Selective Electrode.

FIG. 1E is a sectioned side view of a transflection dip probe.

FIG. 1F is a cross-section of an exploded assembly view of the outer sleeve assembly of FIG. 1E with an Ion Selective Electrode.

FIG. 1G is a cross-section taken through of an assembled instrument of FIG. 1F, showing the inner components of the overall unit fully assembled with an Ion Selective Electrode.

FIG. 2A is a cross-sectional view of a second generation in-situ sample measurement assembly, with distilled water occupying a lowest inner portion.

FIG. 2B is a cross-sectional view of a second generation in-situ sample measurement assembly, with an improved second generation plunger occupying nearly all of the interior volume of the sample assembly and displacing the distilled water of FIG. 2A up to a porous section.

FIG. 2C is a cross-sectional view of a second generation in-situ sample measurement assembly, with an improved Ion Selective Electrode occupying nearly all of the interior volume of the sample assembly.

FIG. 2D is a cross-sectional view of a second generation in-situ sample measurement assembly, with a transflection dip probe occupying nearly all of the interior volume of the sample assembly, and sampling the test solution at the lower end of the sample assembly.

FIG. 2E is a cross-sectional view of a second generation in-situ sample measurement assembly, with a transflection dip probe occupying nearly all of the interior volume of the sample assembly, and sampling the test solution further from the lower end of the sample assembly due to a displacement attachment.

FIG. 4A is a schematic for an optical setup for transflection dip probe measurement of ions in solution.

FIG. 4B is a blow up schematic of a sensitive portion of an optical transflection dip probe measurement of ions in solution.

Figure 1C:
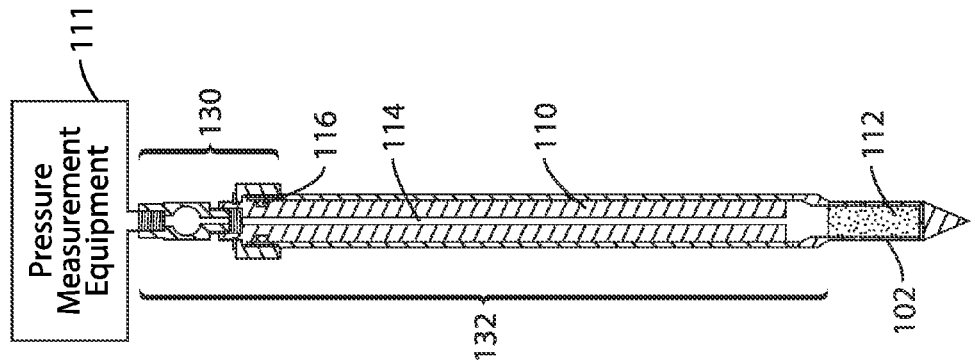
FIG. 1C is a section C-C taken through FIG. 1A, showing the inner components of the overall unit with plunger as assembled.

versus time in hours, where $C_i$ of the inside concentration due to diffusion, and $C_{ave}$ is the average concentration.

DETAILED DESCRIPTION OF THE INVENTION

Referring more specifically to the drawings, for illustrative purposes the present invention is embodied in the apparatus generally shown in FIG. 1A through FIG. 11. It will be appreciated that the apparatus may vary as to configuration and as to details of the parts, and that the method may vary as to the specific steps and sequence, without departing from the basic concepts as disclosed herein.

DEFINITIONS

The following terms are used herein and are thus defined to assist in understanding the description of the invention(s). Those having skill in the art will understand that these terms are not immutably defined and that the terms should be interpreted using not only the following definitions but variations thereof as appropriate within the context of the invention(s).

"Absorbance" (A), in this invention and as used in spectroscopy, is defined as $$A_\lambda = -\log_{10}(I/I_o)$$

where $A_\lambda$ is the absorbance at a specified wavelength $\lambda$, I is the intensity of light that has passed through a sample (transmitted light intensity) and $I_o$ is the original intensity of the light before it enters the sample (the incident light intensity). Absorbance measurements are often carried out in analytical chemistry, since the absorbance of a sample is proportional to the thickness of the sample and the concentration of the absorbing species in the sample, in contrast to the transmittance $I/I_o$ of a solution, which varies logarithmically with thickness and concentration.

"Computer" means any device capable of performing the steps, methods, or producing signals as described herein, including but not limited to: a microprocessor, a microcontroller, a video processor, a digital state machine, a field programmable gate array (FPGA), a digital signal processor, a collocated integrated memory system with microprocessor and analog or digital output device, a distributed memory system with microprocessor and analog or digital output device connected by digital or analog signal protocols.

"Computer readable medium" means any source of organized information that may be processed by a computer to perform the steps described herein to result in, store, perform logical operations upon, or transmit, a flow or a signal flow, including but not limited to: random access memory (RAM), read only memory (ROM), a magnetically readable storage system; optically readable storage media such as punch cards or printed matter readable by direct methods or methods of optical character recognition; other optical storage media such as a compact disc (CD), a digital versatile disc (DVD), a rewritable CD and/or DVD; electrically readable media such as programmable read only memories (PROMs), electrically erasable programmable read only memories (EEPROMs), field programmable gate arrays, (FPGAs), flash random access memory (flash RAM); and information transmitted by electromagnetic or optical methods including, but not limited to, wireless transmission, copper wires, and optical fibers.

"Ion Selective Electrode" (ISE) (also known as a specific ion electrode (SIE)) means a transducer that converts the activity of a specific ion dissolved in a solution into an electrical potential that may be measured by a voltmeter or pH meter. The voltage is theoretically dependent on the logarithm of the ionic activity, according to the Nernst equation. The sensing part of the electrode is usually constructed as an ion-specific membrane, along with a reference electrode. Ion Selective Electrodes are used in biochemical and biophysical research, where measurements of ionic concentration in an aqueous solution are required, usually on a real time basis.

"Solution" generally refers to, but is not limited to, water and any other dissolved or suspended material found in a liquid that may be removed from soil. In one non-limiting example, nitrate ions are present in such solution, and may be measured to determine the amount of nitrate available to plants in a specific location of soil.

"Tensiometer" means a device used to determine soil matric potential $\Psi_m$ (soil water tension) in the vadose zone. The tensiometer consists of a Plexiglas or plastic tube with a porous ceramic cup, and is filled with water. The top of the tube has either a built-in vacuum gauge or a rubber septum used with a portable handheld reading instrument, which uses a hypodermic needle to measure the pressure inside the tensiometer. The tensiometer is buried in the soil, and a pump is used to pull a partial vacuum. As water is pulled out of the soil by plants and evaporation, the vacuum inside the tube increases. As water is added to the soil, the vacuum inside the tube pulls moisture from the soil and decreases. The actual gage reading will vary according to the type of soil, the moisture content, and due to hysteresis, according to the saturation history of the soil.

Tensiometers are used in irrigation scheduling to help farmers and other irrigation managers to determine when to water. In conjunction with a water retention curve, tensiometers can be used to determine how much to water. With practice, a tensiometer can be a useful tool for these purposes. Tensiometers can also be used in the scientific study of soils and plants.

A simpler, but somewhat less precise, description of the tensiometer is a device commonly used to measure water pressure in soil. One tensiometer may be used with other tensiometers to determine the direction of water flow in a soil profile through determination of a soil hydraulic gradient.

"Transflection dip probe" means a device that measures transmission, dispersion, and reflection losses of a solution that it has been dipped or otherwise immersed into. By using such transmission or reflection over a known distance, an absolute concentration of a specific absorptive species may be determined with a calibrated light source and a spectrometer.

INTRODUCTION

Among the soil nutrients for plant growth, nitrogen ($N_2$) is one of the essential macronutrients for crop production, mostly taken up by plants in the form of the nitrate ($NO_3^-$) ion. The absence of in-situ instrumentation limits the ability to monitor concentration levels of soil solution nitrate and to evaluate plant nutrient uptake mechanisms for specific environmental and agricultural management practices.

New in-situ measurement techniques are presented here that may be applied to actual growing crops, with soil nitrate concentration measurements recorded electronically in real time, as opposed to extracting soil solutions for time consuming remote laboratory measurements. Both methods of nitrate measurement described here use a stainless steel solution sampler design comprising a pointed hollow tube or sleeve.

Methods of Nitrate Measurements

One in-situ nitrate measurement technique uses a nitrate ($NO_3^-$) Ion Selective Electrode (ISE) to determine in-situ nitrate concentrations in soil. Laboratory tests have confirmed that by using a one-point calibration procedure, the nitrate ($NO_3^-$) Ion Selective Electrode is able to measure in situ nitrate ($NO_3^-$) ion concentrations in soil solution.

A second in-situ nitrate measurement technique measures nitrate ion concentrations by using transflection dip probes, based on Ultraviolet to Visual (UV-VIS) wavelength absorption spectroscopy. This nitrate sampler has internal optics that enables a beam of light to be directed through the solution in the sampler. Internal optics within the transflection dip probe are coupled to optical fibers that allow light to be transmitted into and out of the sampler, enabling analysis with a portable fiber optic spectrometer.

This invention describes both of the above innovative measurement approaches for use for in-situ nitrate measurements. By analogy, many other soil-borne ion species may be readily measured.

First Generation In-Situ Ion Measurement

Refer now to FIGS. 1A-1G which together detail the construction of a representative in-situ nitrate ($NO_3^-$) or other Ion Selective Electrode measurement system 100. This system comprises three main parts.

First a stainless steel porous section 102 and stainless steel tube 104 are joined by welding 106 or otherwise joining of a transition piece to match diameters. The top 108 of the stainless steel tube 104 is threaded to ensure a pressure tight fitting when inserting two other parts during the measurement process.

Second, a hollow white Delrin® (DuPont's brand name for polyoxymethylene) cylinder 110 is used as a volume limiter (also known as the plunger 110). The sheer volume of the hollow cylinder 110 serves to limit the amount of solution 112 allowed in the solution chamber (formed by the cylinder 110 and the porous section 102). At the center of the plunger 110, a through hole 114 is drilled through the center length to allow excess solution from the porous section 102 to escape upward into the central body of the plunger 110, thus allowing the plunger 110 to be used as a tensiometer in connection with external pressure measurement equipment 111.

Figure 1B:
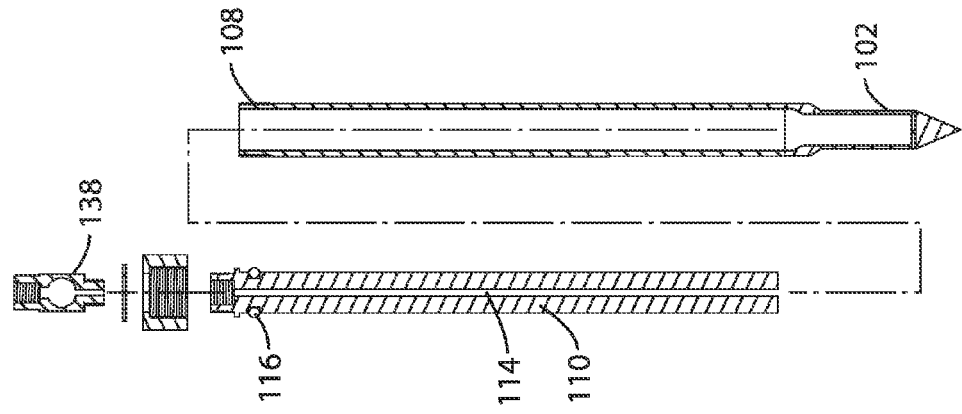
FIG. 1B is a cross-section of an exploded assembly view of the outer sleeve and plunger assembly of FIG. 1A.
Figure 1A:
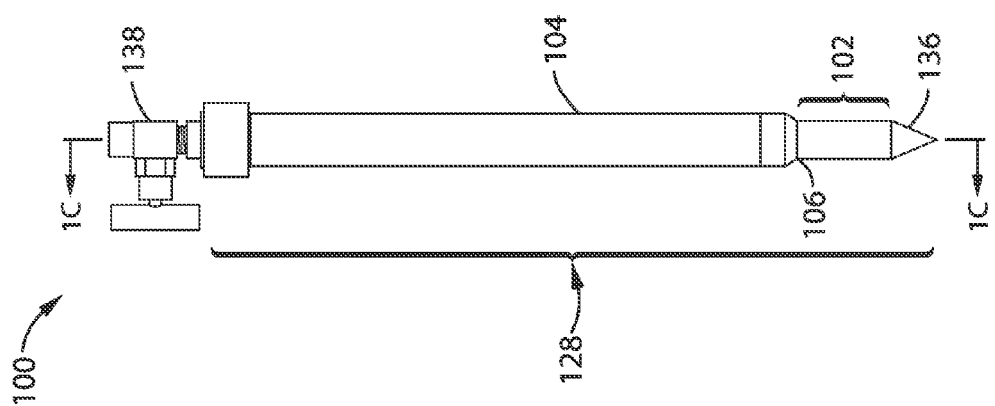
FIG. 1A is a side view of an outer sleeve assembly.

In this manner, the measurement system 100 may be supplied with an extra source of solution until equilibrium is established with surrounding soil conditions. An O-ring seal 116 is provided to seal the plunger 110 to the inner diameter of the stainless steel tube 104, thus restraining fluid flow from one end of the stainless steel tube 104 to the other to pass only through the central hole 114 of the hollow plunger 110. As long as the porous section 102 is completely buried in soil, the overall systems of FIGS. 1A, 1B and 1C are capable of holding a gage vacuum of 700 mbar.

Third, a probe section may comprise either an Ion Selective Electrode (ISE), or an optical probe, either suspended by an inner sleeve tube 118. Referring specifically now to FIGS. 1D, 1E and 1G it is found that the inner sleeve tube 118 may serve to support the Ion Specific Electrode in FIG. 1D or optical probe in FIG. 1E inside in a sealed, waterproof attachment on the interconnect end of the probe.

The inner sleeve tube 118 connects to the distal end 120 through a sealed threaded connection 122 that is waterproof. If it is desired to replace a first Ion Specific Electrode 124 with another Ion Specific Probe, or an optical probe 126, then the inner sleeve tube 118 sleeve is removed the outer sleeve assembly 128 and replaced with a new probe.

The inner sleeve tube 118 connects to the distal end 120 through a sealed threaded connection 122 that is waterproof. If it is desired to replace a first Ion Specific Electrode 124 with another Ion Specific Probe, or an optical probe 126, then the inner sleeve tube 118 sleeve is removed the outer sleeve assembly 124 and replaced with a new probe.

To measure ion concentrations in the soil solution, the outer sleeve assembly 128 depicted in FIG. 1A is first installed in the soil at a desired depth. Then, the porous section 102 of the outer sleeve assembly 128 is filled with a known volume of distilled water. After filling, the white Delrin® plunger 110 is installed within the outer sleeve assembly 128 and sealed with a top cap section 130.

The distal end 120 of the inner sleeve tube 118 is capable of holding different types of Ion Specific Electrodes 124 when different ion species are to be measured in the solution rather than the nitrate ion. Further, a multiplicity of optical probes 126 may be interchanged as well. These probes have in common exposure to any fluid in the porous section 102, thus allowing operation of the sensor portion of the probe.

Any vacuum developed inside the central through-hole 114 of the plunger 110 may be monitored by a suitable vacuum or pressure transducer in fluid connection with the central through-hole 114. After a suitable period of time equilibrating, the ion concentrations within the porous section 102 solution 112 reflect the ion concentrations present in solution in the pore space of the surrounding soil.

When it is initially desired to measure ion concentrations in the porous section 102, the plunger 110 is removed, and the probe with inner sleeve and probe assembly 134 is inserted through the remaining stainless steel tube 104, and into the porous section 102. Thus, any probe thus installed will be sensing the solution 112 in the porous section 102, which is representative of the surrounding soil solution conditions. Thereafter, the optical probe with inner sleeve and probe assembly 134 may be left in place to provide continuous in-situ ion measurements as required.

However, during the measurement of nitrate concentration with an Ion Selective Electrode, the solution 112 of the porous section 102 assembly may be discharged losing the existing equilibrium pressure that exists between the porous section 102 and the surrounding soil. Such a loss of equilibrium pressure may cause a decrease in the solution 112 inside the porous section 102 assembly and may eventually lead to an inability to make any meaningful measurement by Ion Selective electrode. To overcome this potential internal pressure loss problem, a second generation of the probe was developed to prevent loss of solution in the porous section 102 assembly during measurement with either Ion Selective Electrodes or optical probes.

Referring now to the overall designs of FIGS. 1A-1G, it may be seen that a conical section 136 is useful for inserting the overall measurement system 100 into the ground with minimal disturbance of the surrounding soil. Additionally, a valve 138 at the top of the measurement system 100 allows for the introduction of additional distilled water, or alternatively attachment of vacuum or pressure transducers so that operation as a tensiometer of the overall measurement system 100 may be obtained. In place of a valve 138, a pressure fit gland 140 (typically comprising one or more deformable elements, not shown), may be used to seal sample tubes 142 or wires 144 exiting the measurement system 100. Alternatively, a rubber septum (not shown) may more simply replace the top cap section 130.

Second Generation In-Situ Sampler

Refer now to FIGS. 2A through 2E, which detail the construction and operation of the second generation measurement systems 200. The bottom assembly 202 was redesigned to comprise two parts: reservoir cup 204, and porous section 206 (FIGS. 2A and 2B). For measurement operation, about 4 ml of de-ionized or distilled (preferably distilled) water 208 is initially placed into the bottom of reservoir cup 204 (FIG. 2A).

A second generation plunger 210 (not hatched so that the other details may be viewed) is inserted into the bottom assembly 202 through the stainless steel tube 212 that displaces the solution of water 208 initially in the bottom of the reservoir cup 204, up to the porous section 206 level (FIG. 2B). The solution 214 then in the porous section 206 will equilibrate with surrounding soil solution through diffusion and other bulk transport processes that may be present. (Assembly diagrams are not shown here, as the assembly process is very similar to those described in FIGS. 1A-1G, and would merely be repetitive.)

When equilibrium is established between the solution 214 at the porous section 206 level, the second generation plunger 210 is removed from inside the stainless steel tube 212 and the solution 214 eventually resumes its original position 208 in the reservoir cup 204 of FIG. 2A. However, at this point the solution 214 at its initial position 208 is now an ion-bearing solution, representative of the surrounding soil matrix within which it had previously been in contact with.

The ion-bearing solution 208 is then measured by inserting either an Ion Selective Electrode 216 (FIG. 2C) or an optical probe (218 in FIG. 2D or 220 in FIG. 2E). The solution sampler thus is designed in such a way that the ion-bearing solution 208 remains in the reservoir cup 204 during ion measurements with either the Ion Selective Electrode (FIG. 2C) or the optical probe (FIGS. 2D and 2E) measurements. All of these solution samplers were designed to measure ion concentrations in the soil solution 208, however, now different concentrations and types of ions in the soil solution 208 may be measured. Of particular interest, nitrate ion concentrations may now be measured.

It should be noted that the Ion Selective Electrode 216 of FIG. 2C may operate with a reference pellet connected to the reference chemical 222 and an air vent 224. Additionally, the optical probe 218 of FIG. 2D may simply be immersed in the fluid solution 226 to be measured. In another embodiment of FIG. 2E, however, a displacement attachment 230 may protrude from the bottom of the optical probe 220 so as to raise the solution level 228 above the level that would have attained with the design of FIG. 2D. Correspondingly, the sensing volume 232 of FIG. 2E is correspondingly elevated over the prior design of FIG. 2D.

Second Generation In-Situ Ion Selective Electrode Calibration

Ion Selective Electrodes (ISEs) may be used to measure the concentration of a specific ion (without limitation, nitrate) in aqueous samples. The cumbersome calibration procedures of the nitrate Ion Selective Electrode (ISE) were sufficiently time consuming that a less complicated and time consuming procedure was developed. A one-point reference Ion Selective Electrode calibration procedure was therefore developed.

Figure 3:
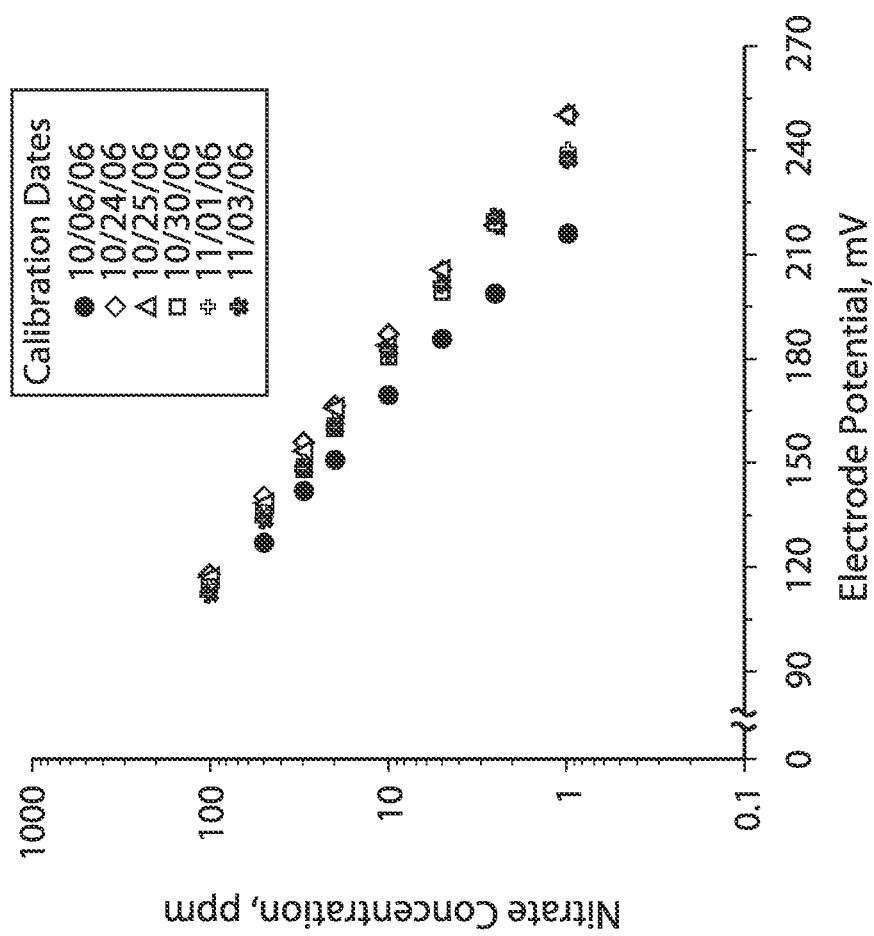
FIG. 3 is calibration plot of ion selective electrode for a standard nitrate aqueous concentration in parts per million (ppm) versus electrode potentials in mV taken over six dates within nearly a month.

Refer now to FIG. 3, which is a data plot of standard nitrate ion concentrations versus Ion Selective Electrode potentials was measured over a period of nearly a month. Eight specific nitrate concentrations were created as standards, over a concentration range from 1 to 100 part per million (ppm). All of the nitrate concentrations were tested on various listed days within the month.

Assuming a stable and constant slope of calibration curves, an averaged slope value was obtained by averaging the slope values from the previous calibrations of FIG. 3. By using the averaged slope value, b, a single point calibration equation was obtained $$C = C_{ref} e^{b(mV - mV_{ref})} \quad (1)$$

where C is the solution concentration (ppm); $C_{ref}$ is the reference solution concentration (ppm); mV is the measured electro-potential of solution (mV); b is the averaged slope; $mV_{ref}$ is the measured electrical potential of a reference solution (mV).

Absorbance Measurements

Refer now to FIGS. 4A and 4B, which are schematics of an overall ion absorption analysis system 400. FIG. 4B is a blow up of a particularly complex region of FIG. 4A. The absorbance measurements (here, nitrate, but suitable modifications could be made for other ions in solution) were made with an ultraviolet-visible (UV-VIS) fiber optic transflection dip probe 402 manufactured by Ocean Optics, 830 Douglas Ave., Dunedin, Fla. 34698, USA. This probe was used in conjunction with the Ocean Optics SD-2000 UV-VIS spectrometer 404 and a Heraeus Fiberlight UV light source 406 (Heraeus Noblelight LLC, Duluth, Ga. 30096, USA). The spectrometer 404 was coupled to a computer 408 for data acquisition and analysis.

The dip probe 402 was in the form of a stainless steel cylinder 410 that contained two optical fibers (illumination source 412 and signal 414) and a lens 416. UV light from the deuterium lamp was directed into the illumination source fiber 412 of the dip probe 402. This illumination source fiber 412 terminated within the probe 402, and the light that exited from the source fiber 412 terminus 418 impinged upon a plano-convex lens 416 located at the end of the stainless steel cylinder 410. This lens 416 directed the light along a path 420 through the liquid 422 (water and ion, calibrated here as with nitrate ions) and onto a surface mirror 424 that was held rigidly in place a fixed distance from the lens 416. The light that was reflected from the mirror 424 returned 426 to the plano-convex lens 416, which focused the return light beam onto the returning signal fiber 414.

The return signal fiber 414 carried light back to the spectrometer 404, allowing the liquid absorption spectra of the liquid 422 to be measured. Although not a limitation, the path length used for the present dip probe configuration was 10 mm.

Nitrate Ion Absorption Characteristics

Figure 5:
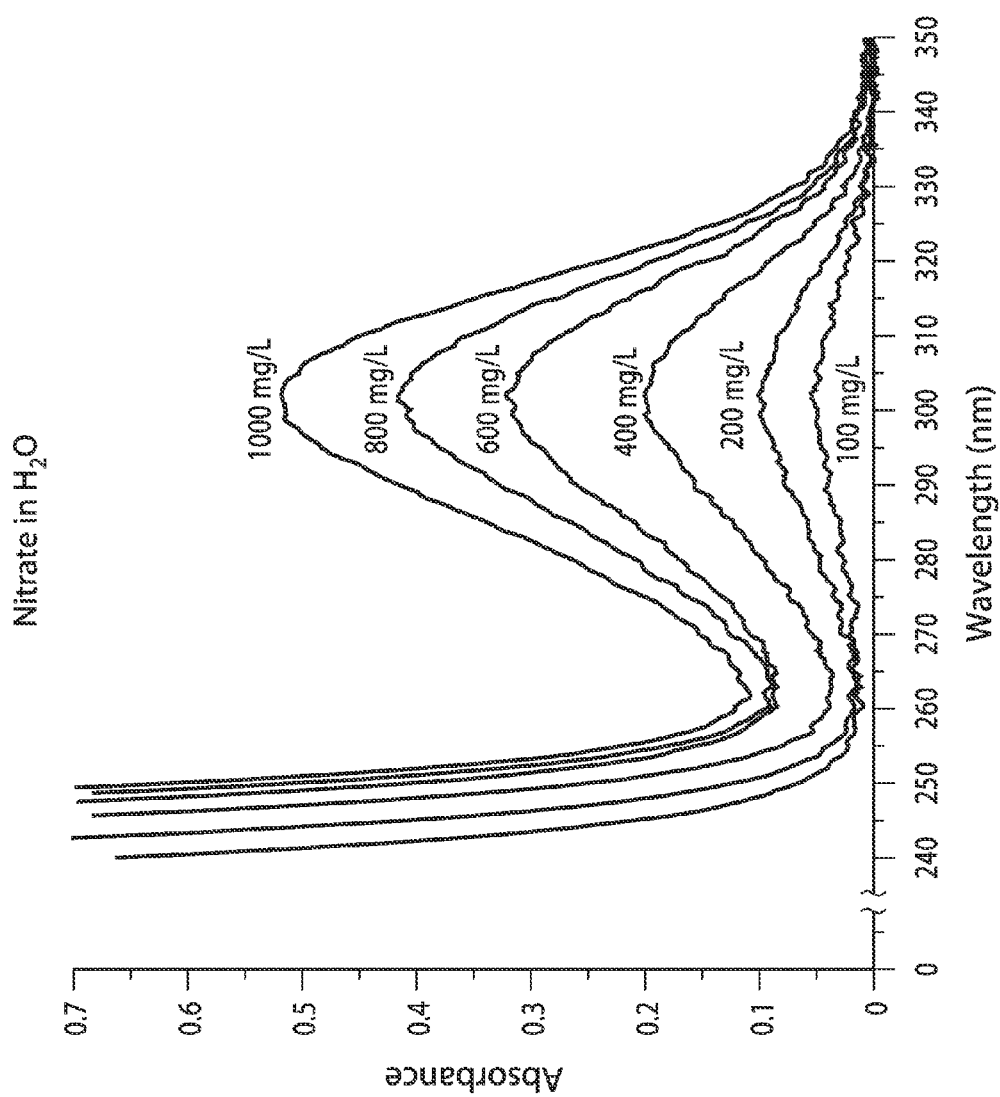
FIG. 5 is a plot of nitrate absorbance between about 250 and 350 nm for different nitrate concentrations.

Refer now to FIG. 5, which is a graph of aqueous nitrate ion absorbance from about 250-350 nm. Regardless of concentration, these plots exhibit two ultraviolet (UV) absorption peaks. A first peak, which is relatively weak, is centered at about 300 nm. A second, much stronger peak is centered at about 210 nm. Both peaks are relatively broad such that useful absorption data may be obtained at wavelengths away from the peaks. The optical system used in these experiments could measure UV-VIS absorption spectra from about 200 nm to 700 nm, and report results from measurements that employed data from the stronger, second UV absorbance peak of nitrate at about 210 nm.

However, it was found that for nitrate loadings as high as 100 ppm, the short-wavelength absorbance values were too high for accurately measuring concentrations for wavelengths less than about 230 nm. Therefore, absorbance spectra at wavelengths in the range 235 nm to 240 nm were used instead. This modified absorbance range provided good results while still allowing strong (but not completely saturated) signals.

Figure 6:
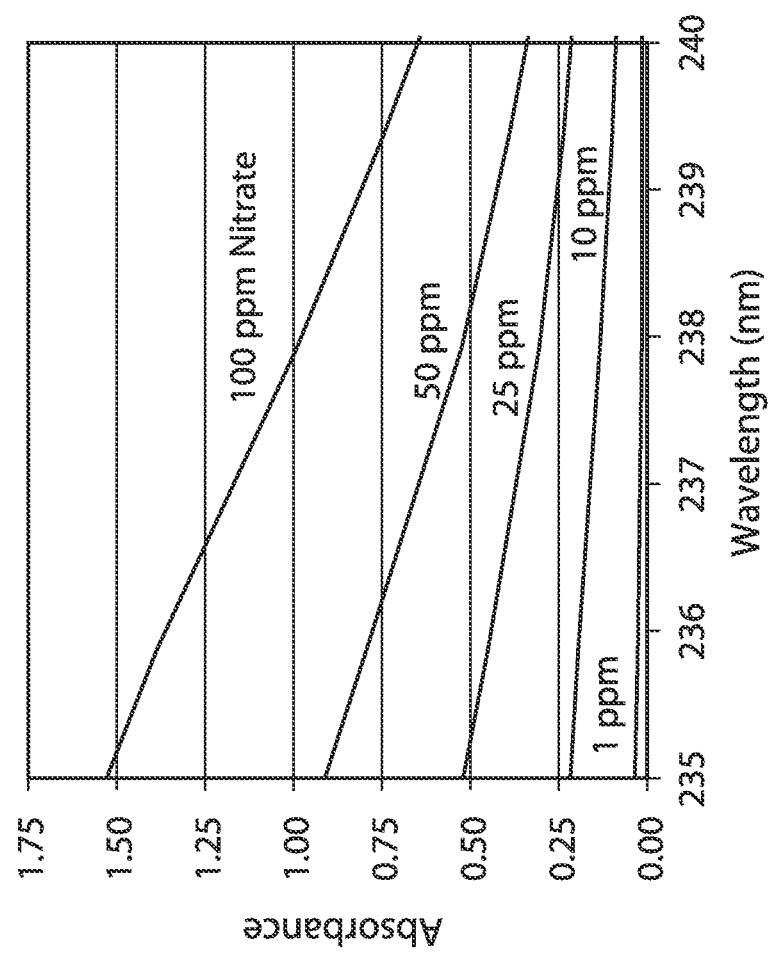
FIG. 6 is a plot of nitrate absorbance versus wavelength in nm for concentrations for 1, 10, 25, 50, and 100 ppm of nitrate.

Refer now to FIG. 6, which graphs nitrate absorbance spectra over the 235-240 nm range for concentrations ranging from 1 to 100 ppm of nitrate. These spectra were obtained by placing the transflection dip probe into nitrate-distilled-water solutions that had been previously prepared. The reference spectrum in each case was deionized water.

Figure 7:
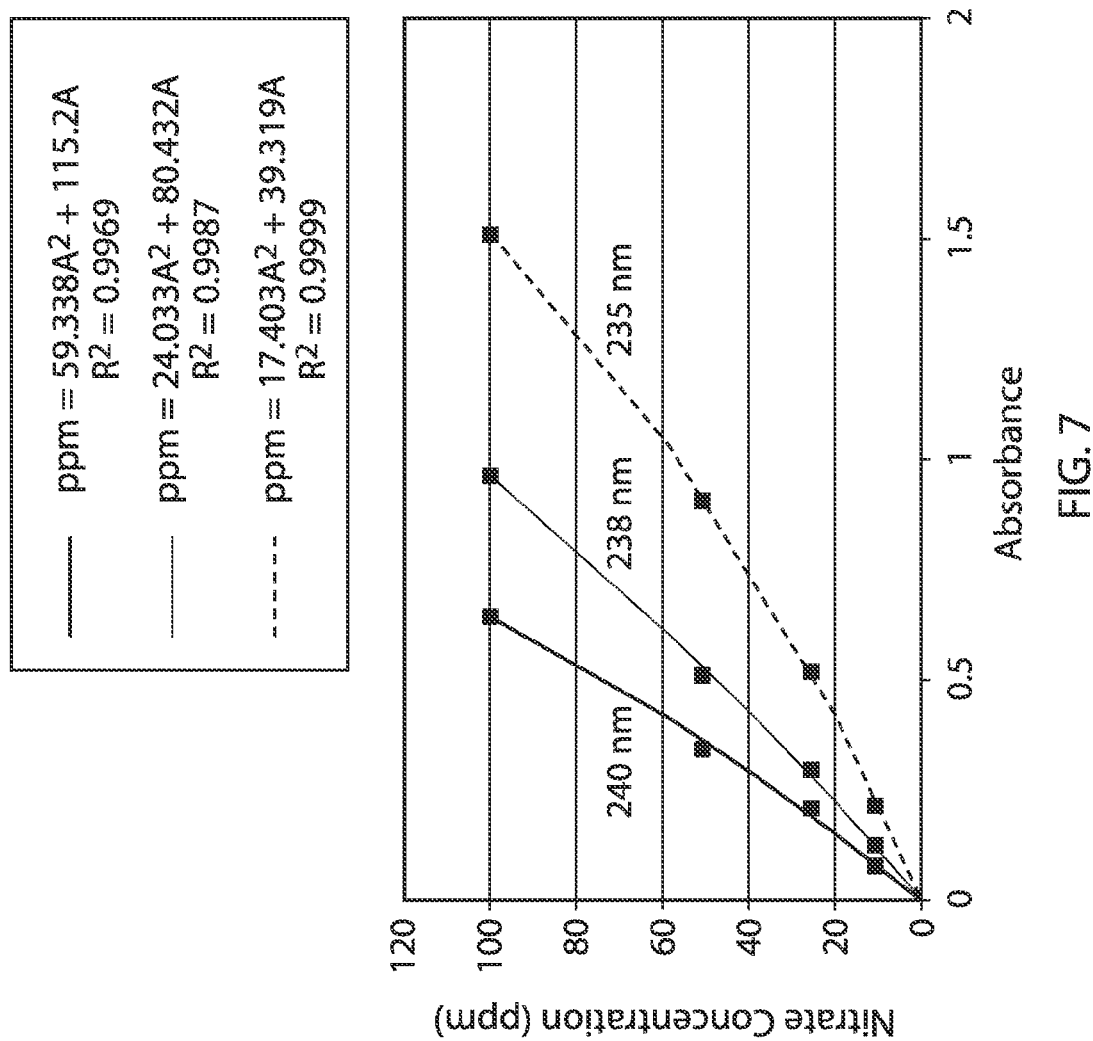
FIG. 7 is a plot of nitrate concentration in ppm versus absorbance at wavelengths of 240, 238, and 235 nm.

Refer now to FIG. 7, which shows plots and quadratic curve fits of calibration data relating absorbance at a given wavelength to the nitrate ion concentration present. FIG. 7 shows calibration data for the wavelengths of 235 nm, 238 nm and 240 nm, with a high degree of correlation (respectively, $R^2=0.9999$, 0.9987, and 0.9969).

Experimental Results—Diffusion Experiments

To test the performance of the in-situ solution sampler, diffusion experiments were conducted at two different water content levels of packed Oso Flaco fine sand (taken from the Oso Flaco sand dunes near Guadalupe, Calif., USA). The first water content had a saturation of 0.434 m$^3$ m$^{-3}$. The second water content was 37 cm suction equivalent water content of 0.347 m$^3$ m$^{-3}$.

To start the experiment with fully saturated conditions, a Büchner funnel was filled with 100 ppm $NO_3^-$ solution. Oso Flaco fine sand was packed around a supported in-situ solution sampler previously described. The resulting bulk density was 1.50 Mg m$^{-3}$. The diffusion experiment at saturation was started by adding 12 ml deionized water into the in-situ solution sampler. The changes in concentration with time were measured with both Ion Selective Electrode and UV-VIS fiber optic transflection dip probes during $NO_3^-$ diffusion from the Oso Flaco soil solution into the sampler solution of both probes.

Figure 8:
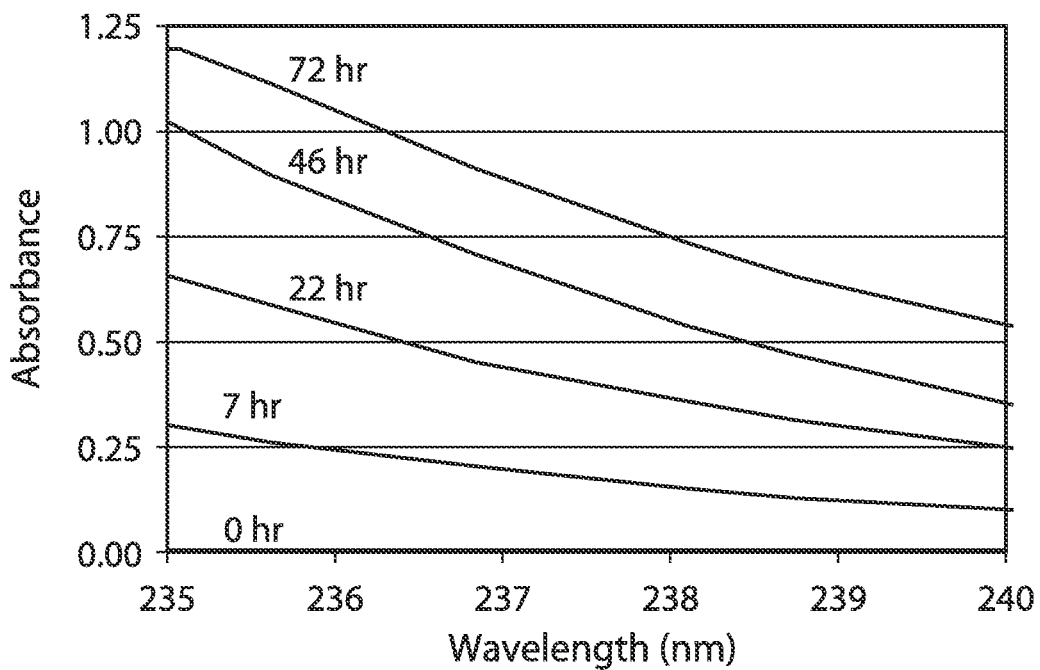
FIG. 8 is a time-varying plot of absorbance versus wavelength in nm from a saturated diffusion experiment over time periods of 0, 7, 22, 46, and 72 hours.

Refer now to FIG. 8, which graphs the results of the time-varying absorption spectra from the saturated diffusion experiment previously described. FIG. 8 shows absorbance spectra at different times, such as 0, 7, 22, 46, and 72 hours.

Figure 9:
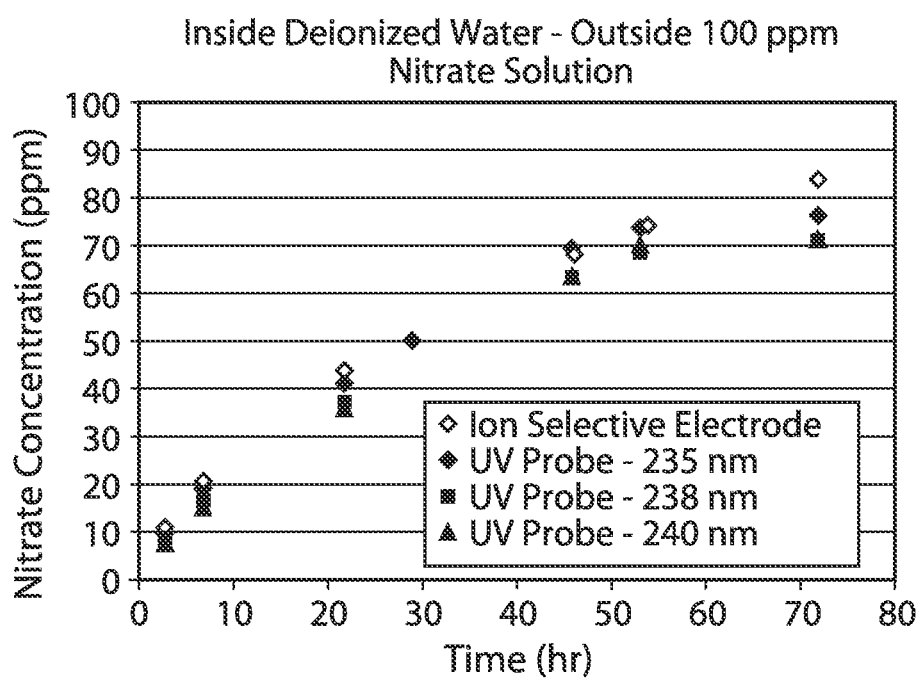
FIG. 9 is a plot of nitrate concentration (ppm) versus time in hours of the inside concentration $C_i$ due to diffusion, with data points for both Ion Selective Electrode and optical transflection dip probe wavelengths of 235, 238, and 240 nm.

Refer to associated FIG. 9, which restates the time-varying nitrate ppm levels measured at wavelengths of 235 nm, 238 nm and 240 nm of FIG. 8. The differences between the data values for these wavelengths are taken to represent the uncertainties in the measurements, which are dependent on the experimental apparatus. Also shown for comparison are experimental data that were obtained using a nitrate Ion Selective Electrode. The data sets are very similar, indicating that both of these independent measurement probes work well, and that the optical probe works equally well at all of the 235 nm, 238 nm and 240 nm wavelengths.

It is also evident from the data of FIG. 9 that the asymptotic value of 100 ppm (the initial bulk surrounding nitrate concentration) would take well in excess of 100 hours to even closely approach. Given the data from FIG. 9, the time constant of the diffusion process (as there is no bulk flow in this experimental setup) could readily be calculated with a least squares curve fit to derived analytical models.

Figure 10:
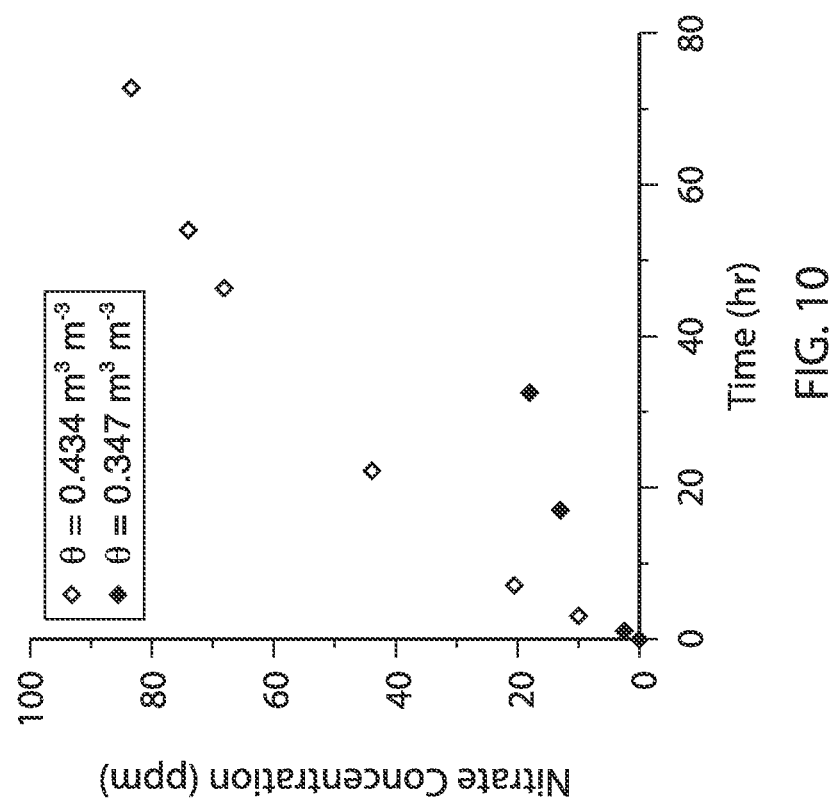
FIG. 10 is a plot of nitrate concentration (ppm in water) versus time in hours of the inside concentration $C_i$ due to diffusion with two different initial soil saturation values, 0.434 $m^3\ m^{-3}$ and 0.347 $m^3\ m^{-3}$.

Refer now to FIG. 10, which is a graph showing the time varying nitrate ion concentration inside the solution sampler as a function of time with two soil water content levels, one with 0.434 m$^3$ m$^{-3}$, and the other at 0.347 m$^3$ m$^{-3}$.

For the experiment with saturated Oso Flaco sand (at 0.434 m$^3$ m$^{-3}$), the nitrate ion concentration measured inside the cup ultimately (beyond the time scale of the graph) increased exponentially close to the final value of 98.44 ppm, as would have been attained theoretically for a homogeneously mixed solution of the same solution volumes.

For unsaturated case (at 0.347 m$^3$ m$^{-3}$), the measured concentrations at equal times were smaller than at saturated conditions. This clearly indicates that the diffusion of nitrate ions through the porous section at saturated conditions is much faster than in unsaturated conditions. This can be attributed to shorter diffusional pathways and cross section areas in the saturated condition.

Model Results—Predicting the Time-Varying Ion Concentrations

A simplified model to predict the time-varying nitrate concentrations inside the porous section can be developed by using simple electric circuit analogies. In this model, average nitrate ion concentrations inside the porous section are denoted $C_i$, and average nitrate concentrations outside the porous section, i.e., in the outer container is $C_o$. In addition, the liquid volumes inside and outside the porous section are denoted as $V_i$ and $V_o$ respectively. For simplicity, the volume of liquid contained within the porous section material itself is assumed to be negligible. The rate, J, that nitrate ions diffuse from the outer volume inside the porous section is given by Equation (2):

$$J = \frac{C_o - C_i}{R_{tot}} \quad (2)$$

where $R_{tot}$ is the overall resistance to mass transfer. In addition, J may be related to the time-rates-of-change of the average concentrations inside and outside the porous section, as shown in Eq. (3):

$$J = V_i \frac{dC_i}{dt} = -V_o \frac{dC_o}{dt} \quad (3)$$

For development of the model here, mass conservation is required in Equation (4):

$$C_i V_i + C_o V_o = C_{ave} V_{tot} \quad (4)$$

By combining Equations (2)-(4) an ordinary differential equation may be formulated, subject to the initial condition $C_i(0)=0$ (imposed due to the initial starting condition, where distilled water was placed into the interior or the porous section $C_i$), which may be solved to result in $C_{ave}=C_o(0)*((1+V_i/V_o)^{-1}$, where $C_i(0)$ and $C_o(0)$ are the nitrate concentrations at the time t=0. After rearranging the solution of the ordinary differential equation, Equation 5 may be obtained $$\ln\left(1 - \frac{C_i}{C_{ave}}\right) = -at \quad (5)$$

such that a plot of ln $$\left(1 - \frac{C_i}{C_{ave}}\right)$$

as a function of time should yield a straight line with the slope −a.

Figure 11:
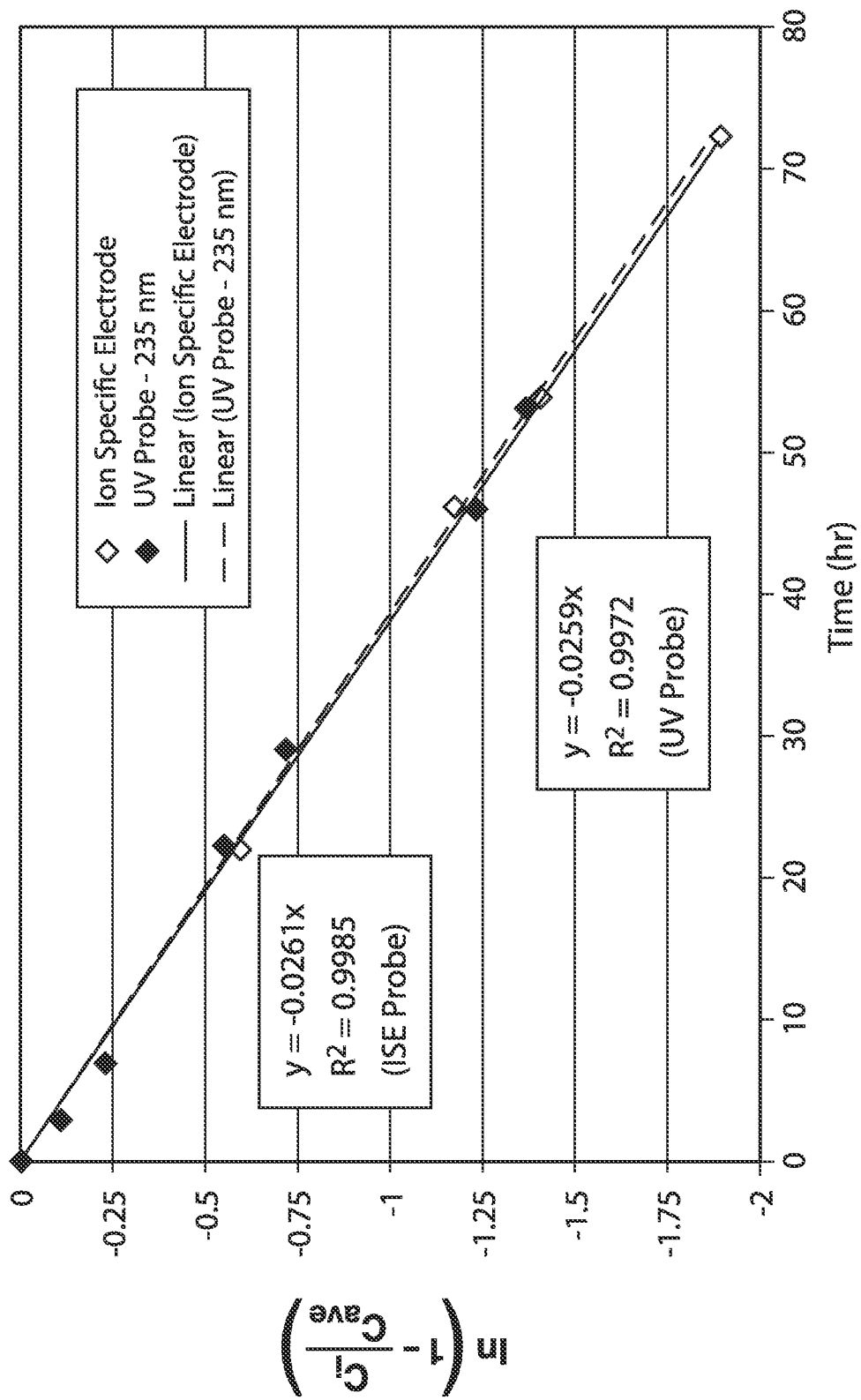
FIG. 11 is a natural logarithmic plot of $$\left(1 - \frac{C_i}{C_{ave}}\right)$$

Experimental data from a diffusion experiment with the region inside the porous section initially filled with deionized water, i.e., with $C_i(0)=0$, are shown in FIG. 11).

Refer now to FIG. 11, which is a plot of ln $$\left(1 - \frac{C_i}{C_{ave}}\right)$$

versus time. It is apparent, then, that the quantity ln $$\left(1 - \frac{C_i}{C_{ave}}\right)$$

varies linearly with time. By measuring the slope of the data, which determines the variable a, the overall resistance to nitrate diffusion, i.e. $R_{tot}$, may be determined by using the definition of the slope a. This overall resistance may be related to the effective diffusion coefficient of porous cup to nitrate by assuming that nitrate diffusion through the wall is quasi-steady, and solving Laplace's equation in cylindrical coordinates $$R_{tot} = \frac{\ln(r_{iw}/r_i)}{2\pi l D_E} \quad (6)$$

Where l is inside height of the porous cylindrical section, $r_{iw}$ is the outside radius, $r_i$ is the inside radius of the porous cup, $D_E$ is the effective diffusion coefficient of the porous cup.

CONCLUSION

Although the description above contains many details, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

What is claimed is:

1. An in-situ ion measurement system, comprising:
 a tube, said tube having a distal end;
 wherein the distal end of said tube comprises a porous section; and
 wherein the porous section comprises pores sized to allow diffusion and bulk fluid flow of a soil solution therethrough to form a measurement solution;
 a probe body having a central bore, said probe body coaxial with said tube; and
 a probe placed within the central bore of the probe body, wherein a sensitive portion of the probe measures at least one characteristic of the measurement solution.

2. The in-situ ion measurement system as recited in claim 1, wherein the probe is an Ion Selective Probe.

3. The in-situ ion measurement system as recited in claim 1, wherein the probe is a nitrate Ion Selective Probe.

4. The in-situ ion measurement system as recited in claim 1, wherein the probe is an optical probe.

5. The in-situ ion measurement system as recited in claim 4, wherein the probe is a transflection dip probe.

6. The in-situ ion measurement system as recited in claim 5, wherein the transflection dip probe allows absorption of an input light source as the input light passes through the measurement solution into an output signal.

7. The in-situ ion measurement system as recited in claim 4, further comprising:
 a deuterium light source that provides an input light source;
 an optical spectrometer that measures an output signal from the passage of the input light source through the measurement solution.

8. The in-situ ion measurement system as recited in claim 7, further comprising:
 a computer that controls a collection of in-situ measurements through the spectrometer.

9. The in-situ ion measurement system as recited in claim 8, further comprising:
 a program executable on the computer, capable of performing steps comprising:
 collecting the in-situ measurements through the spectrometer,
 wherein the in-situ measurements are ion concentration measurements.

10. The in-situ ion measurement system as recited in claim 8, further comprising:
 a program executable on the computer, capable of performing steps comprising:
 collecting the in-situ measurements through the spectrometer,
 wherein the in-situ measurements are nitrate ion concentration measurements.

11. The in-situ ion measurement system as recited in claim 8, further comprising:
 a program executable on the computer, capable of performing steps comprising:
 collecting the in-situ measurements through the spectrometer,
 wherein the in-situ measurements are measured on one or more components of BTEXS concentration measurements.

12. The in-situ ion measurement system as recited in claim 11, wherein BTEXS comprises one or more of a contaminant selected from a group of contaminants consisting of: benzene, toluene, ethyl benzene, xylene, and styrene.

13. The in-situ ion measurement system as recited in claim 7, further comprising:
 a program executable on the computer, capable of performing steps comprising:
 collecting the in-situ measurements through the spectrometer,
 wherein the in-situ measurements are measured on one or more of a contaminant selected from a group of contaminants consisting of: a polychlorinated biphenyl, tetrachloroethylene, sulfur dioxide, arsenic, selenium, petroleum, petroleum distillates, petroleum byproducts, hydrocarbon, pentachlorophenol, creosote, a pesticide, a polycyclic aromatic hydrocarbon (PAH), a volatile organic carbon (VOC), a dioxin, a dibenzofuran, copper, lead, zinc, hexavalent chromium(VI), cadmium, and mercury.

14. The in-situ ion measurement system of claim 1, wherein the porous section comprises a tubular section concentric with the tube.

15. The in-situ ion measurement system of claim 1, wherein the porous section has the same inner and outer diameter as a reservoir cup that terminates in a conical section.

16. An in-situ measurement system, comprising:
 a tube, said tube having a distal end;
 wherein the distal end of said tube comprises a porous section; and
 wherein the porous section comprises pores sized to allow diffusion and bulk fluid flow therethrough;
 a probe body having a central bore;

wherein said probe body is coaxial with said tube;
a solution in material surrounding the probe body that diffuses and flows through the porous section to produce a measurement solution;
a probe placed within the central bore of the probe body, wherein a sensor portion of the probe measures at least one characteristic of the measurement solution; and
a computer that controls a collection of in-situ measurements from the sensor portion of the probe.

17. The in-situ measurement system as recited in claim 16, wherein the probe comprises an Ion Selective Electrode probe.

18. The in-situ measurement system as recited in claim 16, wherein the probe comprises a transflection dip probe.

19. The in-situ measurement system as recited in claim 18, wherein the transflection dip probe is capable of measuring absorbance in the range of 200 nm through 1100 nm.

20. The in-situ measurement system as recited in claim 18, wherein the transflection dip probe is capable of measuring absorbance in the range of 235 nm through 240 nm.

21. The in-situ measurement system as recited in claim 18, wherein the transflection dip probe is capable of measuring solution absorbance at one or more of the wavelengths selected from the group of wavelengths consisting of: 235 nm, 238 nm, and 240 nm.

22. An in-situ ion measurement system, comprising:
a tube, said tube having a distal end;
wherein the distal end of said tube comprises a porous section; and
wherein the porous section comprises pores sized to allow diffusion and bulk fluid flow therethrough;
an in-situ probe body having a central bore;
wherein said probe body is coaxial with said tube;
a soil solution in soil surrounding the probe body wherein the soil solution diffuses and flows through the porous section to form a measurement solution; and
a probe placed within the central bore of the probe body, wherein a sensitive portion of the probe measures at least one characteristic of the measurement solution.

23. The in-situ ion measurement system of claim 22, further comprising:
a deuterium light source, wherein the deuterium light source provides illumination to the sensitive portion of the probe.

24. The in-situ measurement system of claim 22, further comprising:
a spectrometer, wherein the spectrometer provides measurement solution absorption spectra to a computer.

25. The in-situ measurement system of claim 22, further comprising:
a displacement attachment situated on the probe;
wherein the probe is an optical probe, said optical probe having a bottom; and
wherein the displacement attachment protrudes from the bottom of the optical probe;
whereby the optical probe senses the measurement solution.

26. The in-situ measurement system of claim 22, further comprising:
a plano-convex lens that transmits a deuterium light source from an illumination source fiber to a mirror through the measurement solution; and
a returning signal fiber disposed to collect the light reflected through the measurement solution from the mirror and focused by the plano-convex lens.

27. The in-situ measurement system of claim 22, wherein the probe is removable.

* * * * *